United States Patent [19]

Rice

[11] Patent Number: 5,326,926
[45] Date of Patent: Jul. 5, 1994

[54] ISOMERIZATION WITH IMPROVED RVP AND C4 RECOVERY

[75] Inventor: Lynn H. Rice, Palatine, Ill.

[73] Assignee: UOP, Des Plaines, Ill.

[21] Appl. No.: 29,495

[22] Filed: Mar. 11, 1993

[51] Int. Cl.$^5$ ............................................. C07C 5/13
[52] U.S. Cl. ...................................... 585/738; 585/748
[58] Field of Search ................................ 585/738, 748

[56] References Cited

U.S. PATENT DOCUMENTS 4,347,399  8/1982  Rice ........................................ 585/738
5,146,037  9/1992  Zarchy et al. ......................... 585/738

Primary Examiner—Anthony McFarlane
Assistant Examiner—Nhat D. Phan
Attorney, Agent, or Firm—Thomas K. McBride; John G. Tolomei

[57] ABSTRACT

A process for the isomerization of $C_4$–$C_6$ paraffins that separates a low boiling or overhead fraction from a stabilizer in a stripping zone and provides a low RVP isomerization product and simplifies the recovery of LPG components. The process also lowers energy costs and capital investment for recovery of LPG components that are otherwise lost with the production of low RVP isomerization products. When used with a chloride promoted catalyst, the arrangement of this invention permits recovery of a low RVP isomerate product while reducing or eliminating corrosion problems associated with a condensation of overhead products to produce stream containing liquid HCl.

17 Claims, 2 Drawing Sheets

ISOMERIZATION WITH IMPROVED RVP AND C4 RECOVERY

BACKGROUND OF THE INVENTION

This invention relates generally to the isomerization of hydrocarbons. This invention relates more specifically to the isomerization of light paraffins and the separation of the product effluent stream.

DESCRIPTION OF THE PRIOR ART

High octane gasoline is required for modern gasoline engines. Formerly it was common to accomplish octane number improvement by the use of various lead-containing additives. As lead is phased out of gasoline for environmental reasons, it has become increasingly necessary to rearrange the structure of the hydrocarbons used in gasoline blending in order to achieve high octane ratings. Catalytic reforming and catalytic isomerization are two widely used processes for this upgrading.

A gasoline blending pool normally includes $C_4$ and heavier hydrocarbons having boiling points of less than 205° C. (395° F.) at atmospheric pressure. This range of hydrocarbon includes $C_4$-$C_6$ paraffins and especially the $C_5$ and $C_6$ normal paraffins which have relatively low octane numbers. The $C_4$-$C_6$ hydrocarbons have the greatest susceptibility to octane improvement by lead addition and were formerly upgraded in this manner. Octane improvement can also be obtained by using isomerization to rearrange the structure of the paraffinic hydrocarbons into branch-chained paraffins or reforming to convert the $C_6$ and heavier hydrocarbons to aromatic compounds. Normal $C_5$ hydrocarbons are not readily converted into aromatics, therefore, the common practice has been to isomerize these lighter hydrocarbons into corresponding branch-chained isoparaffins. Although the $C_6$ and heavier hydrocarbons can be upgraded into aromatics through hydrocyclization, the conversion of $C_6$'s to aromatics creates higher density species and increases gas yields with both effects leading to a reduction in liquid volume yields. Therefore, it is common practice to charge the $C_6$ paraffins to an isomerization unit to obtain $C_6$ isoparaffin hydrocarbons. Consequently, octane upgrading commonly uses isomerization to convert $C_6$ and lighter boiling hydrocarbons and reforming to convert $C_7$ and higher boiling hydrocarbons.

The isomerization of paraffins is a reversible first order reaction. The reaction is limited by thermodynamic equilibrium. The basic types of catalyst systems that are used in effecting the reaction is a hydrochloric acid promoted aluminum chloride system and a supported aluminum chloride catalyst. Additional catalyst systems that are in use include zeolites.

New requirements for reformulated gasoline have profound impacts on the operation of isomerization as well as reformers. Reformulated gasoline requirements impose limitations on gasoline end points, benzene as well as total aromatics, and reid vapor pressure (RVP). Providing lower RVP fuels or sustaining a given RVP level for a gasoline pool while maintaining octane levels without benzene or aromatics will often impose lower RVP restrictions on the isomerate product.

The requirement of lower RVP isomerate product streams requires the elimination of the lower boiling components from the bottoms fraction of the isomerization zone effluent. Typical components carried away from the bottoms stream of the usual isomerization zone stabilizer comprise mainly $C_4$ and some $C_5$ hydrocarbons. Separation of additional $C_4$ components from the bottoms fraction requires additional pressure and temperature in the bottom of the stabilizer zone. These elevated conditions impose additional energy charges on the process operation.

Taking the additional $C_4$'s and $C_5$'s overhead form the stabilizer zone poses other operational burdens on the process. First the $C_4$'s and $C_5$'s represent higher value fuel or product components that, absent the presence of expensive facilities for their recovery, are lost with the light ends. For example the addition of depropanizer to separate the net overhead stream from the typical will recover the $C_4$'s and $C_5$'s, but only at the expense of significantly increased capital and operating expenses. Furthermore in isomerization zones that use chlorided catalyst systems the $C_4$'s and $C_5$'s raise the dew point of the net stabilizer overhead and can result in a mixed phase overhead stream containing HCl. HCl present in overhead liquid requires more expensive piping and equipment to avoid corrosion problems.

It is an object of this invention to provide a process for the isomerization of $C_4$-$C_6$ hydrocarbons that simplifies the steps and reduces the expense of providing a low RVP product stream.

Another object of this invention is to lower the equipment and operating costs of recovering $C_4$ and $C_5$ hydrocarbons ordinarily separated from a low RVP isomerate product.

A yet further object of this invention is to eliminate mixed phase flow of a net stabilizer overhead stream in an isomerization zone that uses a halogen promoted catalyst.

BRIEF DESCRIPTION OF THE INVENTION

Accordingly, this invention is a process for the isomerization of $C_4$-$C_6$ paraffins that separates a low boiling or overhead fraction from a stabilizer in a stripping zone and provides a low RVP isomerization product. The invention simplifies the recovery of LPG components and lowers energy costs and capital investment for recovery of LPG components that are otherwise lost with the production of low RVP isomerization products. The invention provides added benefits when used with a chloride promoted catalyst. For such catalysts the invention permits recovery of a low RVP isomerate product while reducing or eliminating corrosion problems associated with the condensation of overhead products which produce streams containing liquid HCl.

Accordingly in one embodiment this invention is a process for the isomerization of a feed stream comprising $C_4$-$C_5$ hydrocarbons and separation of the reactor effluent. The invention includes the steps of contacting the feed stream in an isomerization reaction zone with an isomerization catalyst at isomerization conditions to produce an isomerization zone effluent. A portion of the isomerization zone effluent passes to a stabilizer zone for recovering a stabilizer overhead stream comprising $C_4$ and lighter hydrocarbons, a bottoms stream comprising $C_5$ and heavier hydrocarbons and a stripper feed comprising $C_4$ hydrocarbons and lower boiling material. The stripper feed passes to a stripping zone that separates the stripper feed into a stripper overhead stream comprising $C_3$ hydrocarbons and lower boiling material and a stripper bottoms stream comprising $C_4$ hydrocarbons. At least a portion of the stripper overhead stream mixes with a hydrocarbon fraction produced by the stabilizer having a boiling point at or below the boiling point of the stripper feed. A stripper bottoms stream containing $C_4$ and $C_5$ hydrocarbons is withdrawn from said stripping zone.

In another embodiment this invention is a process for the isomerization of a feed stream comprising $C_4$-$C_6$ hydrocarbons and the separation of an isomerization zone effluent. The process comprises mixing hydrogen with the feed stream which may contain $C_4$ hydrocarbons; contacting the feed stream and hydrogen mixture in a reaction zone with an isomerization catalyst comprising alumina, having from 0.01 to 25 wt. % platinum and from 2 to 10 wt. % of a chloride component at isomerization conditions; maintaining a chloride concentration in the reaction zone of from 30 to 300 ppm; recovering an isomerization effluent stream from the reaction zone containing HCl; passing the isomerization zone effluent to a stabilizer column at a feed entry point and recovering a stabilizer overhead stream comprising $C_4$ and lower boiling hydrocarbons and HCl, a bottoms stream comprising $C_5$ and heavier hydrocarbons and a sidecut stream comprising a stripper feed, the stripper feed comprising and lower boiling hydrocarbons and HCl; passing the stripper feed to a stripping column and separating the stripper feed into a stripper overhead stream comprising $C_3$ and lower boiling hydrocarbons and HCl, and a stripper bottoms stream comprising $C_4$ hydrocarbons; returning the stripper overhead stream to the stabilizer column at a location above the feed entry point or to the stabilizer overhead stream; recovering the stripper bottoms stream from the stripping column; and, passing the stabilizer overhead stream to a receiver and recovering an overhead product stream containing HCl and consisting essentially of vapor from the overhead receiver.

Other aspects of this invention relate to feed stream compositions, effluent stream compositions, reactor configurations, hydrogen concentrations, and catalyst details.

DETAILED DESCRIPTION OF THE INVENTION

Figure 1:
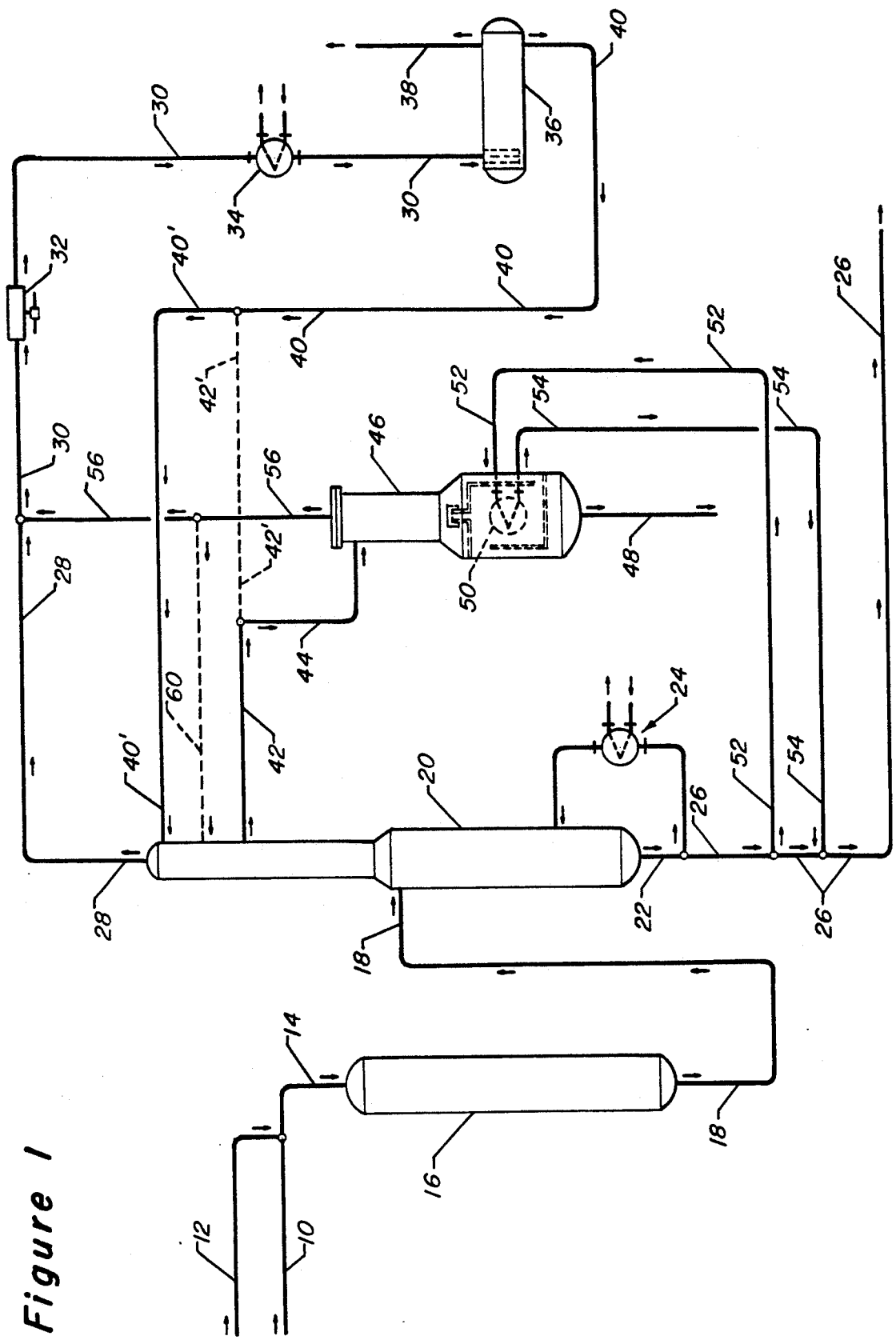
FIG. 1 is a schematic representation of the flow scheme of this invention.

The feedstocks that can be used in this invention include hydrocarbon fractions rich in $C_4$-$C_6$ normal paraffins. The term "rich" is defined to mean a stream having more than 50% of the mentioned component. Preferred feedstocks are substantially pure normal paraffin streams having from 4 to 6 carbon atoms or a mixture of such substantially pure normal paraffins. Other useful feedstocks include light natural gasoline, light straight run naphtha, gas oil condensate, light raffinates, light reformate, light hydrocarbons, field butanes, and straight run distillates having distillation end points of about 77° C. (170° F.) and containing substantial quantities of $C_4$-$C_6$ paraffins. Preferably the effluent from the isomerization zone will contain a substantial amount of $C_4$ hydrocarbons. $C_4$ hydrocarbons concentration of at least 3 mol % are desired and $C_4$ hydrocarbon concentration in the range of from 5 to 20 mol % are preferred. The $C_4$ hydrocarbons in the effluent may be present in the feed entering the isomerization zone or produced by cracking reactions within the isomerization zone. The feed stream may also contain low concentrations of unsaturated hydrocarbons and hydrocarbons having more than 6 carbon atoms. The concentration of these materials should be limited to 10 wt. % for unsaturated compounds and 20 wt. % for heavier hydrocarbons in order to restrict hydrogen consumption and cracking reactions.

Hydrogen is admixed with the feed to the isomerization zone. Although no net hydrogen is consumed in the isomerization reaction, the isomerization zone will have a net consumption of hydrogen often referred to as the stoichiometric hydrogen requirement which is associated with a number of side reactions that occur. These side reactions include saturation of olefins and any remaining aromatics, cracking and disproportionation. Hydrogen in excess of the stoichiometric amounts for the side reactions is maintained in the isomerization zone to provide good stability and conversion by compensating for variations in feedstream compositions that alter the stoichiometric hydrogen requirements and to prolong catalyst life by suppressing the side reactions. Side reactions left unchecked reduce conversion and lead to the formation of carbonaceous compounds, i.e., coke, that foul the catalyst.

It has been found to be advantageous to minimize the amount of hydrogen added to the isomerization zone feedstock. When the hydrogen to hydrocarbon ratio at the effluent of the isomerization zone exceeds about 0.05, it is not economically desirable to operate the isomerization process without the recovery and recycle of hydrogen to supply a portion of the hydrogen requirements. Facilities for the recovery of hydrogen from the effluent are needed to prevent the loss of product and feed components that can escape with the flashing of hydrogen from the isomerization zone effluent. These facilities add to the cost of the process and complicate the operation of the process. The isomerization zone can typically be operated economically with the effluent hydrogen to hydrocarbon ratio as low as 0.05 without adversely affecting conversion or catalyst stability. Accordingly where possible, the addition of hydrogen to the isomerization zone feedstock will be kept to below an amount that will produce a hydrogen to hydrocarbon ratio in excess of 0.05 in the effluent from the isomerization zone. For feeds having a low level of unsaturates, satisfying the stoichiometric hydrogen requirements demand a hydrogen to hydrocarbon ratio for the inlet stream of between 0.03 to 0.1. The arrangement of this invention reduces the loss of $C_4$ and other product hydrocarbons taken by the fuel gas by their separate recovery from the stripping zone. Therefore, a further advantage of this invention in some cases is the use of higher hydrogen to hydrocarbon ratios in the isomerization zone despite the elimination of hydrogen recycle facilities.

The hydrogen and hydrocarbon feed mixture is contacted in the reaction zone with an isomerization catalyst. The isomerization zone uses a solid isomerization catalyst to promote the isomerization reaction. There are a number of different isomerization catalysts that can be used for this purpose. The two general classes of isomerization catalysts use a noble metal as a catalytic component. This noble metal, usually platinum, is utilized on a chlorided alumina support when incorporated into one general type of catalyst and for the other general type of catalyst the platinum is present on a crystalline alumina silicate support that is typically diluted with an inorganic binder. Preferably, the crystalline alumina type support is a zeolitic support and more preferably a mordenite type zeolite. The zeolitic type isomerization catalysts are well known and are described in detail in U.S. Pat. Nos. 3,442,794 and 3,836,597.

The preferred isomerization catalyst for this invention consists of a high chloride catalyst on an aluminum base containing platinum. The aluminum is an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt. % of the platinum. Other platinum group metals may be present in a concentration of from 0.1 to 0.25 wt. %. The platinum component may exist within the final catalytic composite as an oxide or halide or as an elemental metal. The presence of the platinum component in its reduced state has been found most suitable for this process.

The catalyst also contains a chloride component. The chloride component termed in the art "a combined chloride" is present in an amount from about 2 to about 10 wt. % based upon the dry support material. The use of chloride in amounts greater than 5 wt. % have been found to be the most beneficial for this process.

There are a variety of ways for preparing the catalytic composite and incorporating the platinum metal and the chloride therein. The method that has shown the best results in this invention prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of the chloride must be incorporated into the catalyst by the addition or formation of aluminum chloride to or on the platinum-aluminum catalyst base. An alternate method of increasing the halogen concentration in the final catalyst composite is to use an aluminum hydrosol to form the aluminum carrier material such that the carrier material also contains at least a portion of the halogen. Halogen may also be added to the carrier material by contacting the calcined carrier material with an aqueous solution of the halogen acid such as hydrogen chloride, hydrogen fluoride, or hydrogen bromide.

It is generally known that high chlorided platinum-alumina catalysts of this type are highly sensitive to sulfur and oxygen-containing compounds. Therefore, the feedstock must be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$-$C_5$ oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the feed stream by hydrotreating. A variety of commercial dryers are available to remove water from the feed components. Adsorption processes for the removal of sulfur and water from hydrocarbon streams are also well known to those skilled in the art.

Operating conditions within the isomerization zone are selected to maximize the production of isoalkane product from the feed components. Temperatures within the reaction zone will usually range from about 40°–235° C. (100°–455° F.). Lower reaction temperatures are generally preferred since they usually favor equilibrium mixtures of isoalkanes versus normal alkanes. Lower temperatures are particularly useful in processing feeds composed of $C_5$ and $C_6$ alkanes where the lower temperatures favor equilibrium mixtures having the highest concentration of the most branched isoalkanes. When the feed mixture is primarily $C_5$ and $C_6$ alkanes temperatures in the range of from 60° to 160° C. are preferred. When it is desired to isomerize significant amounts of $C_4$ hydrocarbons, higher reaction temperatures are required to maintain catalyst activity. Thus, when the feed mixture contains significant portions of $C_4$-$C_6$ alkanes most suitable operating temperatures are in the range from 145° to 225° C. The reaction zone may be maintained over a wide range of pressures. Pressure conditions in the isomerization of $C_4$-$C_6$ paraffins range from 7 barsg to 70 barsg. Preferred pressures for this process are in the range of from 20 barsg to 30 barsg. The feed rate to the reaction zone can also vary over a wide range. These conditions include liquid hourly space velocities ranging from 0.5 to 12 hr.$^{-1}$, however, space velocities between 1 and 6 hr.$^{-1}$ are preferred.

Operation of the reaction zone with a chlorided catalyst also requires the presence of a small amount of an organic chloride promoter. The organic chloride promoter serves to maintain a high level of active chloride on chlorided type catalysts as low levels are continuously stripped off the catalyst by the hydrocarbon feed. The concentration of promoter in the reaction zone is maintained at from 30 to 300 ppm. The preferred promoter compound is carbon tetrachloride. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

Preferably the isomerization reaction zone has at least two reactors. When two reactors are used the catalyst is usually distributed equally between the two reactors. It is not necessary that the reaction be carried out in two reactors but the use of two reactors confer several benefits on the process. The use of two reactors and specialized valving (not shown) allows partial replacement of the catalyst system without taking the isomerization unit off stream. For the short periods of time during which replacement of catalyst may be necessary, the entire flow of reactants may be processed through only one reaction vessel while catalyst is replaced in the other. The use of two reaction zones also aids in maintaining lower catalyst temperatures. This is accomplished by having any exothermic reaction such as hydrogenation of unsaturates performed in the first vessel with the rest of the reaction carried out in a final reactor stage at more favorable temperature conditions. Various methods of exchanging heat between the effluents and reactor input stream are known to those skilled in the art.

Following any heat exchange with the feed stream or intermediate reactor effluent stream the isomerization zone effluent stream enters separation facilities. The separation facilities divide the reaction zone effluent into a product stream comprising $C_4$ and heavier hydrocarbons and a gas stream which is made up of lighter hydrocarbons and hydrogen. In its most basic components the separation facilities will include a stabilizer zone and stripping zone. The stabilizer zone will include an overhead receiver or accumulator and may consist of one column or several columns. In addition to the stabilizer and stripper the separation facilities may also include facilities for recovery of normal alkanes. Normal alkanes recovered from the separation facilities may be recycled to the isomerization reaction zone to increase the conversion of normal alkanes to isoalkanes.

The stabilizer zone ordinarily consists of single column operated to provide a bottom product stream having an RVP of less than 12 psia. Preferably the RVP of the product stream withdrawn by the method of this invention will be in a range of from 8 to 10 psia. Throughout the column the stabilizer will ordinarily have 30 or more trays with about an equal number of trays above and below the feed entry point of the isomerization effluent into the column. Typically the stabilizer operates in a pressure range of from about 150 to 300 psig and a bottoms temperature of about 250° to 400° F.

Above the isomerization effluent entry point, the stabilizer withdraws an overhead stream containing at least a substantial portion of the lighter isomerization effluent fraction. Conditions at the top of the column regularly include temperatures of about 150° to 200° F. After cooling the overhead stream enters a receiver that provides reflux for the stabilizer zone in a ratio of about 0.5 to 1.0 mols of reflux per mol of feed and a net overhead fraction comprising mainly $C_3$ and lighter hydrocarbons. Where the isomerization zone uses a chloride promoted catalyst the net overhead from receiver will contain HCl and consist essentially of vapor. In most cases an HCl containing overhead will enter a scrubber section that contacts the gas with a suitable treatment solution for neutralizing and/or removing the acidic components. Typically, the treatment solution will be a recirculating caustic. Higher pressure operation of the stabilizer zone permits direct passage of the net overhead through caustic treatment facilities and on to a gas recovery section without further compression. Gas recovered from the scrubber section will usually be used as a fuel.

A portion of $C_4$ and higher boiling hydrocarbons that rise above the feed point of the isomerization effluent into the stabilizer zone pass as a stripper feed into a stripping zone. As a ratio of total vapor leaving the stabilizer the stripper liquid feed will be in a range of 0.5 to 0.20. The stripper feed may be taken directly from the stabilizer zone at any point above the isomerization effluent feed point or may be split a portion of the stabilizer overhead fraction. If the overhead fraction provides the stripper feed, it is preferably split from stabilizer reflux stream. Preferably the stripper feed is taken from the highest possible tray location of the stripping zone or from the overhead or reflux stream. Routinely this invention will operate with the single stabilizer column providing the stripper feed as a sidecut taken from within the upper quarter and more preferably the upper 4 or 5 tray locations of the column or from the overhead reflux to the column.

The stripper column serves to remove light ends and any HCl present in the stripper feed from the $C_4$ and higher hydrocarbons. Using a minimum of ten real trays in the stripper column provides a good separation. Stripper feed customarily enters and upper portion of the stripper column which operates at a temperature and pressure in a range of 150° to 250° F. and 150 to 300 psig. A reboiler, preferably internal, provides heat input to the stripper for maintaining the stripper at the desired temperature and operates to provide a vapor to liquid ratio in a range typically above 0.5, but below 1.0. The reboiler may be internal or external to the stripper and can use any suitable stream for heat input whether internal or external to the process arrangement. The minimum vapor to liquid ratio ensures removal of HCl while the upper bound on the ratio avoids overstripping. Overstripping carries excessive amounts of $C_4$ hydrocarbons overhead and increases the $C_4$ to $C_5$ ratio in the stripper bottoms product. In general the bottoms stream from the stripper provides a mixed $C_4$ and $C_5$ product having a high value relative to the fuel gas of the net stabilizer overhead. Frequently this product stream finds use as an liquified petroleum gas component or an alkylation feed.

Stripper overhead containing light ends and possibly HCl enters the stabilizer zone or is admixed with the stabilizer overhead stream. The only limitation on the return of the stripper overhead stream is that if it reenters the stabilizer zone it enters at or above the withdrawal point for the stripper feed. Thus, the stripper overhead may re-enter the stabilizer column directly above the stripper feed sidecut or may be returned to the stripper overhead.

A basic arrangement for the processing equipment used in this invention can be readily understood by a review of the flow scheme presented in FIG. 1. FIG. 1 and this description makes no mention of many pumps, compressors, receivers, condensers, reboilers, instruments and other well-known items of processing equipment in order to simplify the explanation of the invention.

EXAMPLE 1

FIG. 1 depicts the separation zone of this invention in simplest form and is further described in conjunction with this example. This example is based on engineering calculation and data obtained from operating units.

Referring then to FIG. 1 a feed stream enters the process by line 10 and is admixed with hydrogen from line 12 to provide a feed stream taken by line 14. The feedstream contacts an isomerization catalyst in reactor 16 to produce an isomerization effluent having the relative composition given in Table 1 for line 18.

After heat exchange with the incoming feed (not shown) the contents of line 18 enter a 40 tray stabilizer column 20 at a temperature of temperature of about 260³F., a pressure of about 220 psig and a tray location 21. Stabilizer 20 separates the stabilizer feed into a bottom steam 22, a stripper sidecut stream 42 and a stabilizer overhead 28. Following refluxing of a portion of the bottoms stream 22 through a reboiler 24, the net bottoms having the relative composition given in Table 1 leaves the process through a line 26 at a temperature of about 350° F. and a pressure of about 220 psig.

Line 28 transports the overhead stream at a temperature of about 175° F. at a pressure of about 210 psig into admixture with a stripper overhead stream 58. Condenser 32 and cooler 34 lower the temperature of the combined overhead stream 30 to about 100° F. before it enters a receiver 36. Receiver 36 discharges a net vapor stream 38 which after caustic scrubbing has the composition given in Table 1. Lines 40 and 40' return the condensed portion of the combined overhead to stabilizer 20 at a location above the uppermost tray.

In addition to withdrawal of stabilizer overhead 28, column 20 provides a sidecut 42 that passes to a stripper 46 via a line 44. (Although not practiced in this example, the figure depicts a line 42' that can, in total or in part, provide the stripper feed carried by line 44.) Stripper feed entering by line 44 has a chloride concentration of 100 mol ppm and the composition given in Table 1. The contents of line 44 enters a fifteen tray stripping zone above the first tray at a temperature of about 180° F. and a pressure of about 205 psig. An internal reboiler 50 generates vapor at a vapor to liquid ratio of about 0.5. Lines 52 and 54 provide heat for reboiler 50 by cooling the stabilizer bottoms stream 26. A liquid product stream having a chloride concentration of less than 1 wt. ppm and the composition given in Table 1 exits the bottom of the reboiler by a line 48 at a temperature of about 200° F. and a pressure of about 210 psig. Line 56 withdraws the stripper overhead having a chloride concentration of 200 mol ppm and the relative composition given in Table 1 at a temperature of about 190° F. Line 56 conveys a portion of the remainder of the stripper effluent indirectly back to the stabilizer column via receiver 36. (Again while not used in this example, line 60 can pass all or a portion of the stripper overhead directly back to the stabilizer 20.)

EXAMPLE 2

In order to further demonstrate the advantages of this invention the stripper arrangement, stripper draw points from the stabilizer and pressure and temperature conditions within the stabilizer receiver were varied in a separation zone arrangement of this invention. A feed having the composition given in Table 2 entered the separation zone. The resulting vapor recoveries, isomerate vapor pressures, reboiler duties, and HCl concentrations are set forth in Table 3.

EXAMPLE 3

Figure 2:
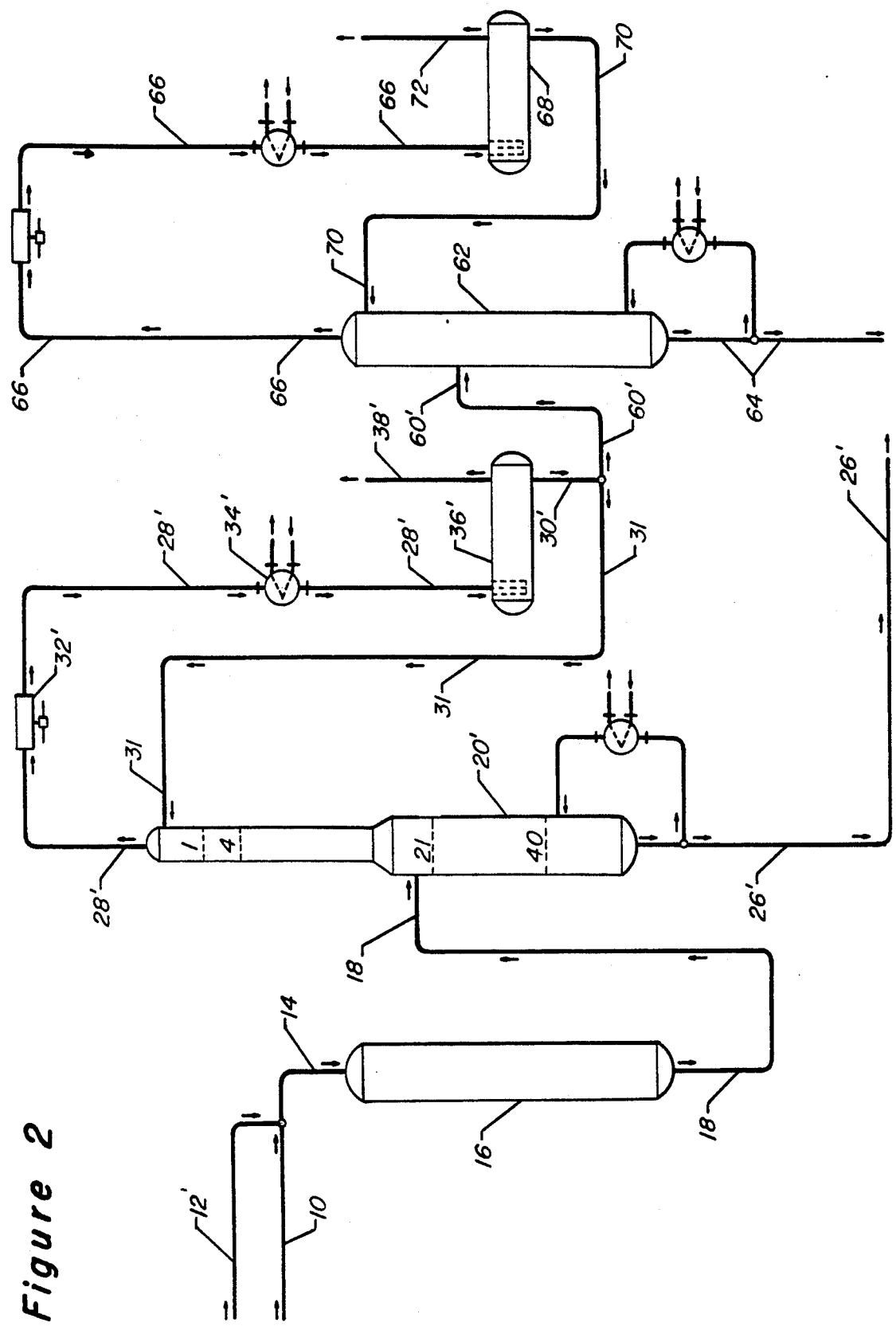
FIG. 2 is a representation of an alternate flow scheme for recovering $C_4$-$C_5$ hydrocarbons from a stabilizer overhead stream.

Example 3 compares the operational and equipment costs associated with the operation of a depropanizer to recover $C_4$ and higher hydrocarbons from the stabilizer overhead with those of this invention. A feed stream having the same composition as that used in Example 2 was passed through the isomerization zone and separation zone arrangement set forth in FIG. 2. Referring then to FIG. 2 the isomerization section operates in essentially the same manner as the that described for FIG. 1. Line 18 in this example passes the effluent from the isomerization zone to a stabilizer column 20' which separates the effluent into a an overhead taken by line 28' and a net bottoms product stream taken by a line 26'. Condenser 32' and cooler 34' cool the overhead stream 28' before it empties into an overhead receiver 36'. A reflux taken by line 30' returns liquid overhead to the stabilizer via a line 31. The product streams from receiver 36' consist of a net vapor stream 38' containing light gases and HCl and a net overhead liquid stream 60' that passes to a depropanizer 62. Depropanizer 62 splits the net overhead 60' into a net bottoms product stream taken by a line 64 and an overhead stream 66. Stream 64 comprises an LPG type product stream containing $C_4$ and a lesser amount of $C_5$ hydrocarbons, which is similar in composition to the net bottoms stream taken by line 48 of FIG. 1. Overhead stream 66, after condensing and cooling passes into an overhead receiver 68. Overhead receiver 69 returns a reflux stream 70 to the column 62 and a net overhead product stream containing light gases and HCl. Table 4 shows the RVP of isomerate product recovered by line 26' and the reboiler duty along with the $C_4$ and $C_5$ composition and HCl concentration of the net bottoms stream 64 for various overhead receiver operating conditions.

A comparison of Examples 2 and 3 demonstrates product recovery advantages as well as operational and equipment savings associated with the use of the stripping zone of this invention as opposed to the depropanizer. Case 5 of Table 3 represents an operation wherein the net stripper bottoms stream 48 provides a recovery of an additional 30 mol pounds per hour (mph) of $iC_4$ and an additional 10 mph of $nC_4$ over a system without the sidecut stripper. Case 1 (Table 4) of the depropanizer arrangement results in the recovery of an additional 7 mph of $iC_4$ and a loss of 1 mph of $nC_4$ relative to Case 5 of Table 3. If $iC_4$ is valued at $0.40 per U.S. gallon and $nC_4$ at $0.35, the sidecut arrangement of this invention results in a relative product savings of over $3,800 per day over a system without LPG recovery. Moreover, the sidecut arrangement provides the product savings at an overall lower reboiler duty that provides a net energy savings and a greatly reduced capital cost. The capital cost of the 15 tray stripping column and its associated equipment is approximately ⅓ of the cost of the depropanizer addition.

TABLE 1

| STREAM INDEX COMPONENT NAME | 18 | 26 | 38 | 44 | 48 | 56 |
|---|---|---|---|---|---|---|
| HCl | .00 | .03 | .29 | .00 | .00 | .00 |
| $H_2$ | 4.56 | .00 | 40.4 | .10 | .00 | .16 |
| $C_1$ | 1.39 | .00 | 12.29 | .12 | .00 | .21 |
| $C_2$ | .08 | .00 | .69 | .03 | .00 | .05 |
| $C_3$ | 2.63 | .20 | 23.20 | 6.67 | .00 | 10.86 |
| $IC_4$ | 2.96 | 57.17 | 18.75 | 59.68 | .11 | 61.40 |
| $NC_4$ | 1.18 | 37.60 | 3.50 | 30.83 | .33 | 26.08 |
| $IC_5$ | 10.60 | 4.00 | .01 | 2.28 | 12.07 | 1.10 |
| $NC_5$ | 3.82 | .40 | .00 | .22 | 4.37 | .09 |
| CP | .73 | .00 | .00 | .00 | .83 | .00 |
| 22DMB | 12.76 | .10 | .00 | .05 | 14.59 | .02 |
| 23DMB | 5.01 | .00 | .00 | .00 | 5.73 | .00 |
| 2MP | 15.61 | .03 | .00 | .01 | 17.86 | .00 |
| 3MP | 9.00 | .00 | .00 | .00 | 10.30 | .00 |
| $NC_6$ | 7.65 | .00 | .00 | .00 | 8.76 | .00 |
| MCP | 11.03 | .00 | .00 | .00 | 12.62 | .00 |
| CH | 7.99 | .00 | .00 | .00 | 9.4 | .00 |
| BZ | .00 | .00 | .00 | .00 | .00 | .00 |
| 22DMP | 2.86 | .00 | .00 | .00 | 3.27 | .00 |
| $N_2$ | .10 | .00 | .88 | .00 | .00 | .00 |
| 3MH | .00 | .00 | .00 | .00 | .00 | .00 |

TABLE 2

| COMPONENT NAME | STABILIZER FEED FROM FEED BOTTOMS LBMOL/HR |
| --- | --- |
| HCl | 0.65 |
| $H_2$ | 92.82 |
| $C_1$ | 29.81 |
| $C_2$ | 2.18 |
| $C_3$ | 96.63 |
| $IC_4$ | 99.08 |
| $NC_4$ | 21.11 |
| $IC_5$ | 231.06 |
| $NC_5$ | 92.10 |
| CP | 44.29 |
| 22DMB | 203.74 |
| 23DMB | 86.85 |
| 2MP | 284.37 |
| 3MP | 173.40 |
| $NC_6$ | 118.78 |
| MCP | 252.59 |
| CH | 186.70 |
| 22DMP | 61.33 |

TABLE 3

SIDECUT STRIPPER

| CASE | STAB RECEIVER (36) PSIG | STAB RECEIVER (36) °F. | STAB RECEIVER (36) R/F | VAPOR STREAM (38) MPH $C_4$ | VAPOR STREAM (38) MPH $C_5$ | ISOMERATE (26) TRUE VAPOR PRESSURE PSIA (100° F.) | SIDECUT STRIPPER (46) DRAW | SIDECUT STRIPPER (46) TRAYS | SIDECUT STRIPPER (46) V/L | TOTAL REBOILER DUTIES MMBTU/HR | LPG STREAM (48) MPH $C_4$ | LPG STREAM (48) MPH $C_5$ | HCl WT PPM HCl WT PPM |
| --- | --- | --- | --- | --- | --- | --- | --- | --- | --- | --- | --- | --- | --- |
| 1 | 180 | 120 | 0.8 | 120.1 | 8.4 | 8.5 | — | — | — | 23.0 | — | — | — |
| 2 | 200 | 100 | 0.5 | 72.4 | 0.1 | 8.6 | 5 | — | — | 18.3 | 40.9 | 2.6 | 38 |
| 3 | 200 | 100 | 0.5 | 72.9 | 0.1 | 8.7 | 5 | 5 | 0.5 | 18.3 | 40.1 | 3.2 | 0.016 |
| 4 | 200 | 100 | 0.5 | 72.8 | 0.1 | 8.7 | 5 | 10 | 0.4 | 18.3 | 40.2 | 2.3 | 0.001 |
| 5 | 200 | 100 | 0.5 | 72.9 | 0.1 | 8.7 | 5 | 10 | 0.5 | 18.3 | 40.3 | 3.5 | 0.0002 |
| 6 | 200 | 100 | 0.5 | 73.0 | 0.1 | 8.7 | 5 | 10 | 0.6 | 18.3 | 39.6 | 4.2 | 0.00004 |
| 7 | 200 | 100 | 0.5 | 74.0 | — | 8.7 | 10 | 10 | 0.5 | 18.3 | 37.4 | 6.5 | 0.0001 |
| 8 | 200 | 100 | 0.5 | 75.3 | — | 8.9 | 15 | 10 | 0.5 | 18.2 | 27.4 | 17.2 | 0.0001 |
| 9 | 300 | 100 | 0.5 | 33.3 | — | 8.9 | 5 | 10 | 0.5 | 23.3 | 73.0 | 1.8 | 0.0004 |

TABLE 4

DEPROPANIZER

| CASE | STAB RECEIVER (36') PSIG | STAB RECEIVER (36') °F. | STAB RECEIVER (36') R/F | DEPROPANIZER RECEIVER (68) PSIG | DEPROPANIZER RECEIVER (68) °F. | DEPROPANIZER RECEIVER (68) R/F | VAPOR STREAM (38') MPH $C_4$ | VAPOR STREAM (38') MPH $C_5$ | ISOMERATE (26') TRUE VAPOR PRESSURE PSIA (100° F.) | TOTAL REBOILER DUTIES MMTBU/HR | DEPROPANIZER BOTTOMS (64) MPH $C_4$ | DEPROPANIZER BOTTOMS (64) MPH $C_5$ | DEPROPANIZER BOTTOMS (64) MPH HCl (WT PPM) |
| --- | --- | --- | --- | --- | --- | --- | --- | --- | --- | --- | --- | --- | --- |
| 1 | 200 | 100 | 0.5 | 150 | 100 | 1.0 | 70.8 | 1.2 | 8.6 | 20.0 | 46.0 | 2.5 | 0.0000003 |
| 2 | 300 | 100 | 0.5 | 175 | 100 | 1.2 | 40.9 | 0.4 | 8.6 | 26.5 | 76.7 | 2.5 | 0.0000003 |

What is claimed is:

1. A process for the isomerization of a feed stream comprising $C_4$-$C_6$ hydrocarbons and separation of a reactor effluent, said process comprising:

(a) contacting a feed stream comprising $C_4$-$C_6$ hydrocarbons in an isomerization reaction zone with an isomerization catalyst at isomerization conditions to produce an isomerization zone effluent;

(b) passing at least a portion of said isomerization zone effluent to a stabilizer zone and recovering from said stabilizer a stabilizer overhead stream comprising $C_4$ and lighter hydrocarbons, a bottoms stream comprising $C_5$ and heavier hydrocarbons and a stripper feed comprising $C_4$ hydrocarbons and lower boiling material;

(c) passing said stripper feed to a stripping zone and separating said stripper feed into a stripper overhead stream comprising $C_3$ hydrocarbons and lower boiling material and a stripper bottoms stream comprising $C_4$ hydrocarbons;

(d) mixing at least a portion of said stripper overhead stream with a hydrocarbon fraction produced by said stabilizer having a boiling point at or below the boiling point of said stripper feed; and, (e) recovering said stripper bottoms stream from said stripping zone.

2. The process of claim 1 wherein said hydrocarbon fraction comprises said stabilizer overhead stream.

3. The process of claim 1 wherein said stabilizer zone comprises a single column and said stripper feed comprises a sidecut taken from said stabilizer at a location above a feed point for said isomerization effluent stream.

4. The process of claim 1 wherein said isomerization catalyst includes a chloride promoter material.

5. The process of claim 1 wherein the feed stream to said isomerization zone has a hydrogen to hydrocarbon ratio of less than 0.05.

6. The process of claim 1 wherein said feed stream has a hydrogen to hydrocarbon ratio of more than 0.05 and hydrogen is recovered from said isomerization zone effluent before passing said effluent to said stabilizer zone.

7. The process of claim 1 wherein said stabilizer operates at a pressure in a range of from 150 to 300 psig.

8. The process of claim 1 wherein said stabilizer bottoms stream has an Reid Vapor Pressure in range of from 8 to 10 psia.

9. The process of claim 1 wherein said stabilizer overhead stream passes to an overhead receiver and a receiver overhead stream consisting essentially of vapor is withdrawn from said receiver.

10. The process of claim 1 wherein said isomerization zone effluent comprises at least 3 mol % $C_4$ hydrocarbons.

11. A process for the isomerization of a feed stream comprising $C_4$-$C_6$ hydrocarbons and the separation of an isomerization zone effluent, said process comprising:
  (a) mixing hydrogen with a feed stream comprising $C_4$-$C_6$ hydrocarbons;
  (b) contacting said feed stream and hydrogen mixture in a reaction zone with an isomerization catalyst comprising alumina, having from 0.01 to 25 wt. % platinum and from 2 to 10 wt. % of a chloride component at isomerization conditions;
  (c) maintaining a chloride concentration in the reaction zone of from 30 to 300 ppm;
  (d) recovering an isomerization effluent stream from said reaction zone containing HCl and at least 5 mol % $C_4$ hydrocarbons;
  (e) passing said isomerization zone effluent to a stabilizer column at a feed entry point and recovering a stabilizer overhead stream comprising $C_4$ and lower boiling hydrocarbons and HCl, a bottoms stream comprising $C_5$ and heavier hydrocarbons and a sidecut stream comprising a stripper feed, said stripper feed comprising $C_4$ and lower boiling hydrocarbons and HCl;
  (f) passing said stripper feed to a stripping column and separating said stripper feed into a stripper overhead stream comprising $C_3$ and lower boiling hydrocarbons and HCl, and a stripper bottoms stream comprising $C_4$ hydrocarbons;
  (g) returning said stripper overhead stream to said stabilizer column at a location above said feed entry point or to said stabilizer overhead stream;
  (h) recovering said stripper bottoms stream from said stripping column; and,
  (i) passing said stabilizer overhead stream to a receiver and recovering an overhead product stream containing HCl and consisting essentially of vapor from said overhead receiver.

12. The process of claim 11 wherein said sidecut is taken from said stabilizer at a location above said feed entry point for said isomerization effluent stream.

13. The process of claim 11 wherein the feed stream to said isomerization zone has a hydrogen to hydrocarbon ratio of less than 0.05.

14. The process of claim 11 wherein said feed stream has a hydrogen to hydrocarbon ratio of more than 0.05 and hydrogen is recovered from said isomerization zone effluent before passing said effluent to said stabilizer column.

15. The process of claim 11 wherein said stripper column is reboiled with bottoms from said stabilizer column.

16. The process of claim 11 wherein said stabilizer operates at a pressure in a range of from 150 to 300 psig.

17. The process of claim 11 wherein said stabilizer bottoms streams has an Reid Vapor Pressure in range of from 8 to 10 psia.

* * * * *